United States Patent
Atherton et al.

(10) Patent No.: US 7,933,649 B1
(45) Date of Patent: Apr. 26, 2011

(54) IMPLANTABLE CARDIAC STIMULATION DEVICE AND METHOD FOR MEASURING INTRINSIC ACTIVITY METRICS IN MULTI-SITE PACING

(75) Inventors: Adam F. Atherton, Saugus, CA (US); Xing Pei, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 497 days.

(21) Appl. No.: 11/222,722

(22) Filed: Sep. 8, 2005

(51) Int. Cl.
*A61N 1/362* (2006.01)

(52) U.S. Cl. ............................................. 607/9

(58) Field of Classification Search .................... 607/27, 607/28
See application file for complete search history.

(56) References Cited

U.S. PATENT DOCUMENTS

| | | | | |
|---|---|---|---|---|
| 4,515,161 A | * | 5/1985 | Wittkampf et al. | 607/27 |
| 5,683,431 A | * | 11/1997 | Wang | 607/28 |
| 5,902,324 A | * | 5/1999 | Thompson et al. | 607/9 |
| 6,081,748 A | * | 6/2000 | Struble et al. | 607/9 |
| 6,144,880 A | * | 11/2000 | Ding et al. | 607/23 |
| 6,148,234 A | * | 11/2000 | Struble | 607/28 |
| 6,456,878 B1 | * | 9/2002 | Yerich et al. | 607/9 |
| 6,456,880 B1 | | 9/2002 | Park et al. | 607/25 |
| 6,668,194 B2 | * | 12/2003 | VanHout | 607/9 |
| 6,748,261 B1 | | 6/2004 | Kroll et al. | 600/510 |
| 2005/0125041 A1 | * | 6/2005 | Min et al. | 607/9 |

* cited by examiner

*Primary Examiner* — Carl H. Layno
*Assistant Examiner* — Jon-Eric C. Morales

(57) ABSTRACT

An implantable cardiac stimulation device provides measurement of intrinsic heart activity metrics while sustaining pacing of the heart. The device includes a pulse generator that delivers pacing pulses to a first chamber of corresponding chambers of a heart, and a sensing circuit that senses a conducted evoked response of a second chamber of the corresponding chambers of the heart in response to the pacing pulse to provide an electrical signal representing the conducted evoked response. The device further includes a measuring circuit that measures a metric of the electrical signal to approximate a corresponding metric of an intrinsic electrical feature of the second chamber.

20 Claims, 3 Drawing Sheets

IMPLANTABLE CARDIAC STIMULATION DEVICE AND METHOD FOR MEASURING INTRINSIC ACTIVITY METRICS IN MULTI-SITE PACING

FIELD OF THE INVENTION

This invention relates generally to a programmable cardiac stimulation device and method for measuring intrinsic activity metrics in multi-site pacing. More specifically the present invention relates to a biventricular stimulation device providing measurement of intrinsic electrical features.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Recently, there has been the introduction of pacing systems that stimulate in corresponding chambers of the heart as, for example, the right ventricle (RV) and left ventricle (LV). These are termed biventricular stimulation devices.

Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat.

Biventricular pacing has been found to be particularly advantageous in patient's suffering from congestive heart disease because of the improved ability of the left ventricle to fully pump blood from the heart. As a result, patients are able to tolerate greater exertion, have a longer life span, and experience a higher quality of life.

Biatrial pacing has also been suggested to lend in coordinating contractions of the right and left atria. As used herein, the term corresponding chambers is meant to refer to either the right and left atria or the right and left ventricle.

With the ability to pace either or both sets of corresponding heart chambers, it is believed that a wide variety of irregularity of heart rhythms may be most efficiently addressed. For example, in a patient suffering from dilated cardiomyopathy, typically the left ventricle is predominately affected in the earlier stages of the disease. The dilated left ventricle has diminished contractility causing its contraction to be slower and weaker than the still healthy right ventricle. Thus, by selecting the stimulation pathway direction from the left ventricle to the right ventricle, the slower left ventricle contraction is initiated prior to the faster right ventricle contraction, yielding superior synchronization of right ventricle and left ventricle contractions.

Determining intrinsic signal amplitudes is essential for implantable pacemaker and defibrillator devices. Currently, such evaluations generally take the form of manual sense tests performed by an external programmer. Automatic sense tests may also be performed periodically by the device itself. In the future, there will also be a need for automatic sensitivity adjustment, in addition to these measurement tests.

These tests have historically been performed by reducing the pacing rate and waiting for intrinsic activity. However, measurement of intrinsic signal amplitude with traditional methods becomes extremely difficult in patients lacking frequent intrinsic activity. It is even more difficult in patients with a biventricular device typically programmed for triggered continuous pacing. The measurements are often frustrating. More importantly, patients may feel uncomfortable due to long escape intervals. If these measurements are to be made without changing the therapy, then automatic R-wave measurements may be extremely difficult, if not impossible.

As will be seen subsequently, the present invention addresses these and other issues. More particularly, and according to an embodiment of the invention, metrics of intrinsic electrical cardiac activity may be measured without upsetting existing pacing therapy in patients lacking intrinsic activity or when overdrive pacing is recommended.

SUMMARY

What is described herein is an implantable cardiac stimulation device comprising a pulse generator that delivers pacing pulses to a first chamber of corresponding chambers of a heart, and a sensing circuit that senses a conducted evoked response of a second chamber of the corresponding chambers of the heart in response to a pacing pulse delivered to the first chamber of the heart to provide an electrical signal representing the conducted evoked response which mimics the intrinsic signal. The device further comprises a measuring circuit that measures a metric of the electrical signal to approximate a corresponding metric of an intrinsic electrical feature of the second chamber.

The pulse generator may be arranged to deliver pacing pulses to a ventricle of the heart. Further, the pulse generator may be arranged to deliver pacing pulses to both of the corresponding chambers in a bi-chamber pacing mode. The corresponding chambers may be the right ventricle and the left ventricle or the right atrium and left atrium.

The intrinsic electrical feature may be an R wave. The metric may be an amplitude of the electrical signal, as for example, the R wave. The amplitude may be a peak amplitude of the electrical signal. The metric may alternatively or additionally be a conduction time from the pacing pulse to a peak amplitude of the electrical signal. The device may further comprise a memory that stores a value of the measured metric.

The pulse generator may be arranged to repeatedly vary one of amplitude and width of the pacing pulses delivered to the first chamber. The measuring circuit may then be arranged to correspondingly repeatedly measure the metric of the electrical signal.

The invention may further provide an implantable cardiac stimulation device comprising a pulse generator that delivers pacing pulses to a first ventricle of a heart, and a sensing circuit that senses a conducted evoked response of a second ventricle of the heart in response to a pacing pulse delivered to the first ventricle of the heart to provide an electrical signal representing the conducted evoked response which mimics the intrinsic signal. The device further comprises a measuring circuit the measures a metric of the electrical signal to approximate a corresponding intrinsic R wave metric of the first ventricle.

The invention further provides a method for use in an implantable cardiac stimulation device for approximating a metric of intrinsic heart activity of a given chamber of a heart. The method comprises delivering pacing pulses to a first chamber of the heart, the first chamber being a corresponding chamber with respect to the given chamber of the heart, sensing a conducted evoked response of the given chamber of the heart in response to a pacing pulse delivered to the first chamber of the heart to provide an electrical signal representing the conducted evoked response which mimics the intrinsic signal, and measuring a metric of the electrical signal to approximate the metric of the intrinsic heart activity of the given chamber.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
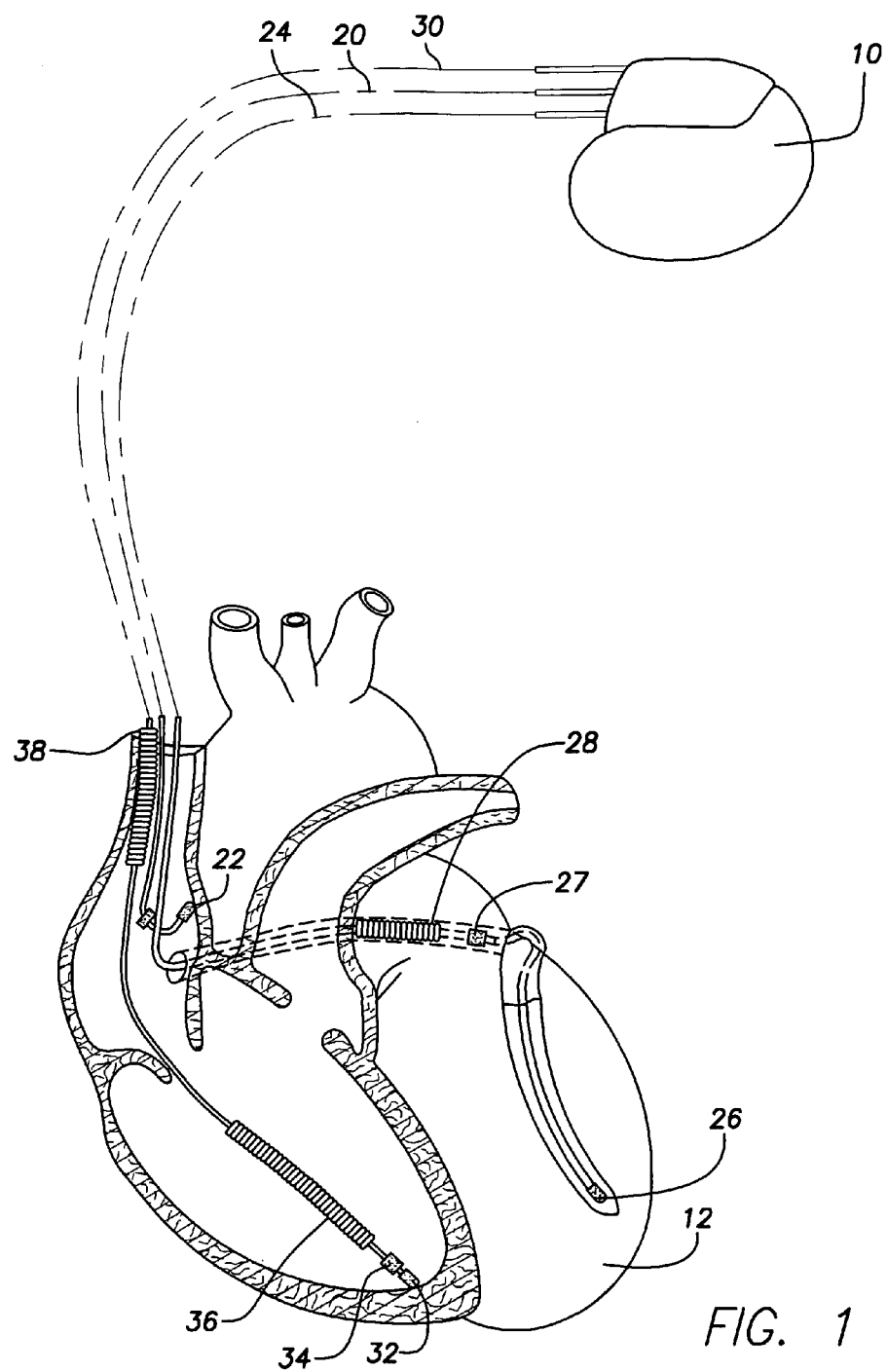
FIG. 1 is a simplified diagram illustrating an implantable stimulation device according to an embodiment of the invention in electrical communication with a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing to the right ventricle and shock therapy to the heart.

Figure 2:
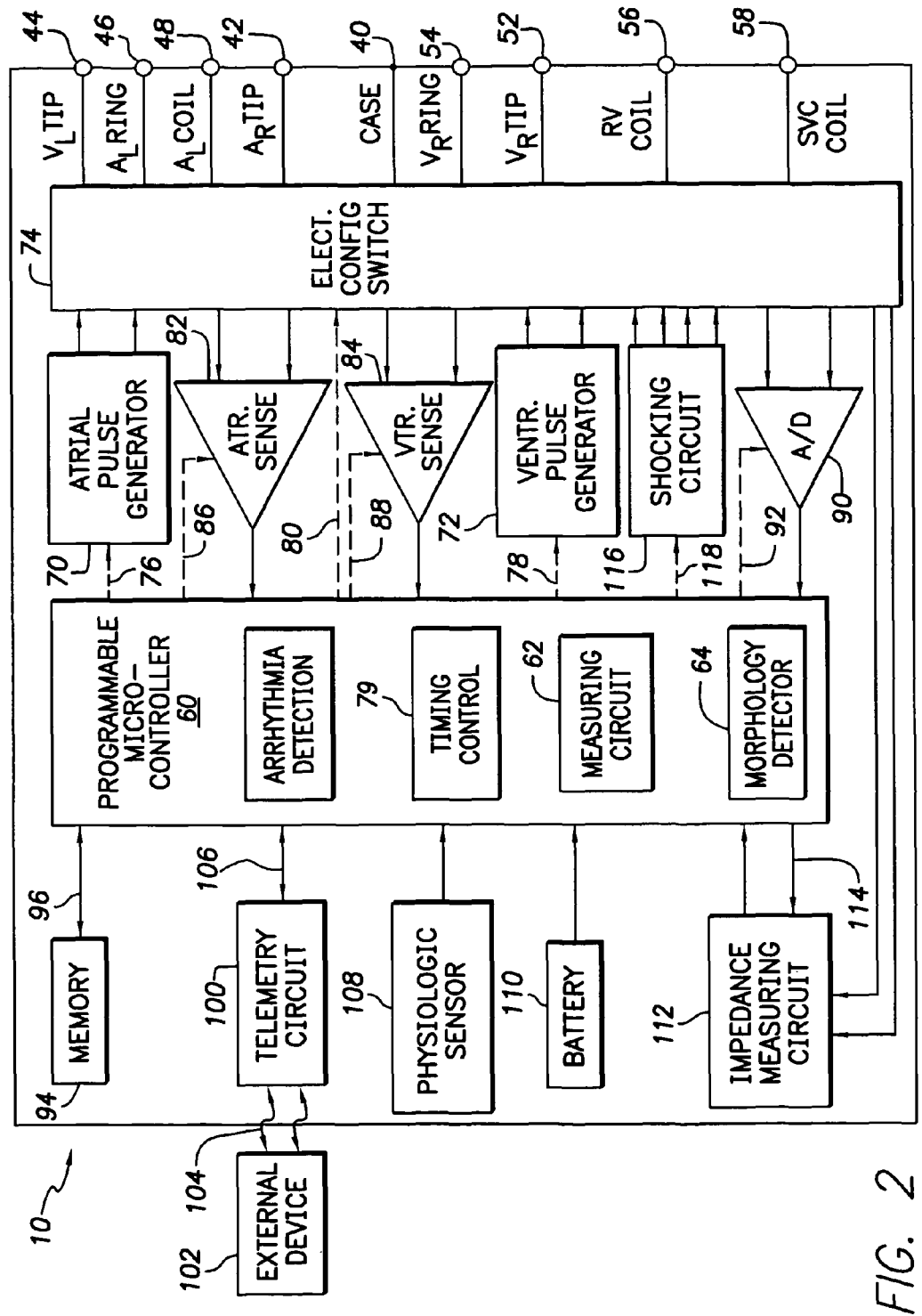
FIG. 2 is a functional block diagram of the implantable stimulation device of FIG. 1.

As illustrated in FIG. 2, a simplified block diagram is shown of the multi-chamber implantable stimulation device 10 according to an embodiment of the present invention, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing and pacing and shocking delivery with vectors using electrodes in the left heart, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing and pacing and shocking delivery with vectors using electrodes in the right heart, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to sense cardiac activity to acquire intracardiac electrogram signals (IEGMs), convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. As will be seen subsequently, the data acquisition system 90 may be coupled to appropriate electrodes and used for sensing a conducted evoked response of a second heart chamber in response to an applied stimulus to a first and corresponding heart chamber. The IEGM thus acquired may then be used for measuring heart activity metrics approximating corresponding metrics of intrinsic activity of the second chamber. The corresponding chamber may be the ventricles, for example, with the first chamber being the left ventricle and the second chamber being the right ventricle. The measured metrics may be, for example, amplitudes, such as peak R wave amplitudes, or time periods, such as conduction times from the applied stimulus, such as a pacing pulse, to the peak R wave amplitude. Still further, stimulation parameters, such stimulation energy or pulse width may be continuously varied and the metrics correspondedly and repeatedly measured to determine the effects resulting from the varied parameters.

With continued reference to FIG. 2, it will be noted that the device 10 further includes a measuring circuit 62 and a morphology detector 64. The morphology detector 64 may be utilized for isolating those features of the IEGM signals having the metric or metrics to be measured. Morphology detectors capable of providing this function are known in the art.

The measuring circuit 62 may, according to this embodiment, measure the metrics of interest. As previously mentioned, the metrics may be, for example, peak R wave amplitudes and conduction times. Other metrics may also be of interest as may be appreciated by those skilled in the art.

The microcontroller 60 is further coupled to a memory 94 by a suitable data/address bus 96, wherein programmable operating parameters used by the microcontroller 60 may be stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. The memory 94 may also be used to temporarily store the conducted evoked response IEGMs and, more permanently, the measured metric values for later analysis and/or use.

The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

According to this embodiment, conducted evoked responses of one chamber (an evoked response resulting from a paced event in the opposite and corresponding chamber) are used to approximate intrinsic activity of the one chamber. Conducted evoked responses of a chamber can represent normal R-waves of that same chamber since it is transmitted through the tissue globally. The resulting conducted evoked response signal should correlate to the intrinsic signal in the ventricle. Hence, the conducted evoked response might also be referred to as the "far-field R-wave that results from a paced event in the opposite chamber". Traditionally, it is difficult, if not impossible, to use a paced evoked response for measuring the amplitudes of intrinsic activities. That is, there is no basis for the "paced evoked response" to correlate to the intrinsic signal. However, with bi-ventricular/multi-site pacing, when pacing in one ventricle/one-site and sensing in the other ventricle/other-site, the conducted evoked response detected in the opposite non-paced chamber will be at least similar to the intrinsic contraction events of the non-paced chamber (site) and hence may be used to approximate the intrinsic activity of the non-paced chamber (site).

Thus, according to this embodiment, the measurement of a conducted R wave in a heart chamber can be considered equivalent to the measurement of the intrinsic events in that same chamber or site. For example, when pacing in the right ventricle or the left ventricle only (referred to as the 'paced chamber') and sensing in the other ventricle (referred to as the 'sensed chamber'), the conducted evoked response in the sensed chamber can be considered to be equivalent to an R wave in the sensed chamber. Using bi-ventricular pacing system and a method embodying the invention, the clinician may now avoid modifying patient therapy, i.e. changing the pacing rate, changing from atrioventricular to ventricular pacing, etc., for the sole purpose of determining R wave amplitudes. It can provide an opportunity to determine the signal amplitudes even when patients lack any intrinsic activities and have only infrequent pre-mature contractions.

Figure 3:
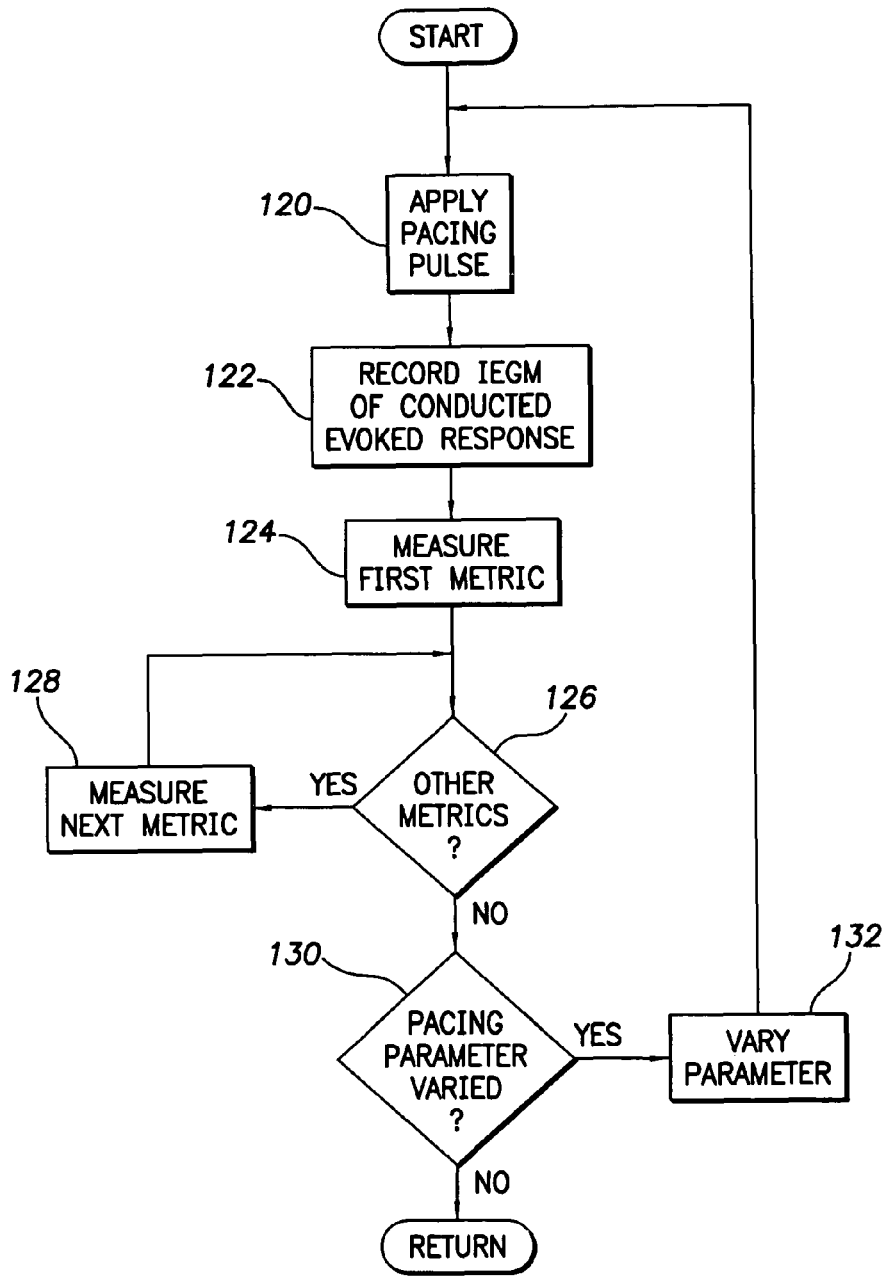
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with an activity block 120. Here, a pacing pulse is applied to one chamber of corresponding chambers. In accordance with this embodiment, the chamber receiving the pacing pulse is the left ventricle. However, as may be appreciated, the chamber receiving the pulse could alternatively be the right ventricle. Furthermore, the present invention is not limited to strictly biventricular pacing. It could, for example, be utilized to advantage in biatrial pacing as well and as may be appreciated by those skilled in the art.

Upon delivery of the pacing pulse to the left ventricle in accordance with activity block 120, the process then immediately advances to activity block 122 wherein the data acquisition system 90 senses cardiac activity in the right ventricle for sensing the conducted evoked response from the pacing pulse delivered to the left ventricle. The data acquisition system 90, upon sensing the conducted evoked response in the right ventricle generates an IEGM signal representing the conducted evoked response and stores the same in memory 94. After the IEGM of the conducted evoked response is stored, the morphology detector 64 and measuring circuit 62 combine to measure a first metric of the conducted evoked response. The first metric may be the peak amplitude of the evoked response, for example. After the first metric is measured in accordance with activity block 124, the process advances to decision block 126 where it is determined if there are other metrics to be measured. If there are, the process then advances to activity block 128 for measuring the next metric of the conducted evoked response. The metric to be measured in accordance with activity block 128 may be, for example, the conduction time from the delivery of the pacing pulse to the left ventricle to the peak amplitude of the conducted evoked response. When all of the metrics are measured, the process then advances to activity block 130 wherein it is determined if the pacing parameters are to be varied. Under some circumstances, it may be desirable to vary the pacing parameters, such as pacing output or pacing pulse width incrementally over a number of cardiac cycles to determine the effect on the measured metrics of the conducted evoked responses. If pacing parameters are to be varied, the process advances to activity block 132 wherein the pacing parameter or parameters are varied and the process then returns to activity block 120 wherein the next pacing pulse is applied to the left ventricle. If there are no pacing parameters to be varied, the process then returns. The metric or metrics, as they are measured, may of course be stored in memory 94 for later analysis and use.

The measured metrics such as evoked response amplitude and conduction time of the conducted evoked response will approximate corresponding metrics of R wave amplitude and conduction time for intrinsic activity of the right ventricle. As a result, intrinsic R wave features may be measured without the need for varying pacing therapy delivered to a patient.

By virtue of the present invention, important information may be gathered which otherwise has not been obtainable. For example, by measuring the peak amplitude of the conducted evoked response, the peak R wave amplitude of the sensing chamber is now known. This can be used in the critical application of discriminating between a normal R wave and a premature ventricular contraction, for example. Such discrimination is particularly important in being able to avoid pacing during a T wave of the heart.

As previously mentioned, the present invention may be extended to the atria as well wherein the corresponding chambers would be the left and right atria. With the present invention extended to the atria, amplitudes of intrinsic atrial activity may be measured to determine atrial sensitivity, for example, in patients with silent sinus node.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.)

What is claimed is:

1. An implantable cardiac stimulation device comprising:
   a pulse generator that delivers pacing pulses to a first chamber of corresponding left and right chambers of a heart;
   a sensing circuit that senses a conducted evoked response in a second one of the left and right chambers opposite the first chamber in response to a pacing pulse delivered to the first chamber of the heart to provide an electrical signal representing the conducted evoked response; and
   a measuring circuit that measures a metric of the electrical signal to approximate a corresponding metric of an intrinsic signal in the second chamber.

2. The device of claim 1, wherein the pulse generator is arranged to deliver pacing pulses to a ventricle of the heart.

3. The device of claim 1, wherein the pulse generator is arranged to deliver pacing pulses to both of the corresponding chambers in a bi-chamber pacing mode.

4. The device of claim 1, wherein the corresponding chambers are a right ventricle and a left ventricle.

5. The device of claim 4, wherein the intrinsic electrical feature is an R wave.

6. The device of claim 1, wherein the metric is an amplitude of the electrical signal.

7. The device of claim 6, wherein the metric is a peak amplitude of the electrical signal.

8. The device of claim 1, wherein the metric is a conduction time from the pacing pulse to a peak amplitude of the electrical signal.

9. The device of claim 1, further comprising a memory that stores a value of the measured metric.

10. The device of claim 1, wherein the pulse generator is arranged to repeatedly vary amplitude and/or width of the pacing pulses delivered to the first chamber and wherein the measuring circuit is arranged to correspondingly repeatedly measure the metric of the electrical signal.

11. An implantable cardiac stimulation device comprising:
    a pulse generator that delivers pacing pulses to a first ventricle of a heart;
    a sensing circuit that senses a conducted evoked response of a second ventricle of the heart in response to a pacing pulse delivered to the first ventricle of the heart to provide an electrical signal representing the conducted evoked response; and
    a measuring circuit that measures a metric of the electrical signal to approximate a corresponding intrinsic R wave metric of the first ventricle.

12. The device of claim 11, wherein the pulse generator is arranged to deliver pacing pulses to a left ventricle of the heart.

13. The device of claim 11, wherein the pulse generator is arranged to deliver pacing pulses to both ventricles of the heart in a bi-ventricular pacing mode.

14. The device of claim 11, wherein the corresponding chambers are a right ventricle and a left ventricle.

15. The device of claim 11, wherein the metric is an amplitude of the electrical signal.

16. The device of claim 11, wherein the metric is a conduction time from the pacing pulse to a peak amplitude of the electrical signal.

17. In an implantable cardiac stimulation device, a method of approximating a metric of intrinsic heart activity, the method comprising:

delivering pacing pulses to a first chamber of the heart, the first chamber being one of a corresponding left or right chamber of the heart;

sensing a conducted evoked response of in a second one of the left or right chambers opposite the first chamber in response to a pacing pulse delivered to the first chamber of the heart to provide an electrical signal representing the conducted evoked response; and measuring a metric of the electrical signal to approximate the metric of the intrinsic heart activity of the given chamber.

18. The method of claim 17, wherein delivering pacing pulses comprises delivering pacing pulses to a ventricle of the heart.

19. The method of claim 17, wherein measuring a metric comprises measuring an amplitude of the electrical signal.

20. The method of claim 17, wherein measuring a metric comprises measuring a conduction time from the pacing pulse to a peak amplitude of the electrical signal.

\* \* \* \* \*